Figure 1:
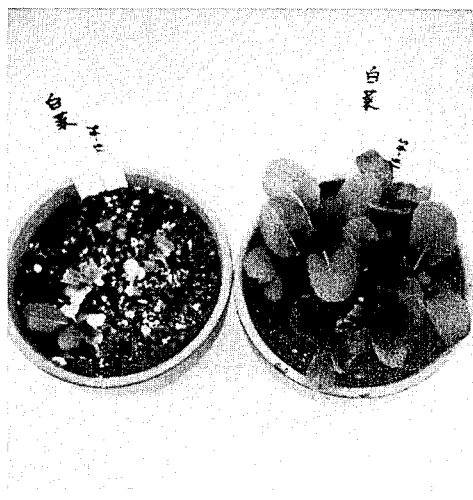

United States Patent [19]

Azuma et al.

[11] Patent Number: 4,772,314

[45] Date of Patent: Sep. 20, 1988

[54] PLANT GROWTH PROMOTER AND METHOD OF PLANT GROWTH PROMOTION

[75] Inventors: Shizuo Azuma; Toshiyuki Hiramatsu; Koji Nakagawa; Teizo Yamaji, all of Iwakuni; Yataro Ichikawa, Tokorozawa, all of Japan

[73] Assignee: Teijin Limited, Osaka, Japan

[21] Appl. No.: 838,617

[22] Filed: Mar. 12, 1986

[30] Foreign Application Priority Data

Mar. 14, 1985 [JP] Japan .................................. 60-49218
Dec. 4, 1985 [JP] Japan ................................ 60-271310

[51] Int. Cl.$^4$ .............................................. A01N 37/44
[52] U.S. Cl. ........................................ 71/111; 71/115; 71/118
[58] Field of Search ......................... 71/115, 111, 118

[56] References Cited

U.S. PATENT DOCUMENTS

| | | | |
|---|---|---|---|
| 2,734,216 | 2/1956 | Wood et al. | 71/115 |
| 3,436,206 | 4/1969 | Kinoshita et al. | 71/77 |
| 4,246,426 | 1/1981 | Van Daele | 71/115 X |

OTHER PUBLICATIONS

Sytdik et al., Chem. Abst., vol. 87 (1977), 48865j.

Primary Examiner—Catherine L. Mills
Attorney, Agent, or Firm—Wenderoth, Lind & Ponack

[57] ABSTRACT

A plant growth promoter comprising as an active ingredient for plant growth promotion at least one phenylglycine selected from the group consisting of
(1) monomeric phenylglycines,
(2) N-phenylglycylphenylglycines, and
(3) cyclic dimers of phenylglycines.

2 Claims, 2 Drawing Sheets

PLANT GROWTH PROMOTER AND METHOD OF PLANT GROWTH PROMOTION

This invention relates to a plant growth promoter and a method of growth promotion. More specifically, it relates to a plant growth promoter comprising a phenylglycine as an active ingredient for plant growth, and to a plant growth promoting method.

Various active compounds have been proposed for growth promotion, increased harvest, increased fruit size, etc. of crops. One example is a plant hormone isolated from a naturally occurring material. It is extremely difficult however to obtain such a natural isolate in great quantities, and its synthesis costs are very high. On the other hand, attempts have been made to promote plant growth by using artificially synthesized compounds, and it is known that certain aminocarboxylic acids or their derivatives have a stimulating or promoting effect on the growth of plants.

West German Laid-Open Patent Publication No. 2217896 describes that L-methionine, DL-methionine and their esters or salts are effective for increasing fruit size, harvest, carbohydrate content, etc.

U.S. Pat. No. 3,564,010 describes that aliphatic carboxylic acids represented by the following formula

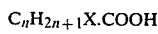

$C_nH_{2n+1}X.COOH$ wherein n is an integer of 5 to 8 and X is the group

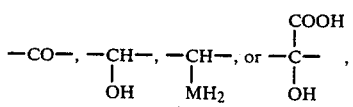

such as alpha-hydroxy-alpha-hexylmalonic acid or its salt, ester or amide have activity on the growth or metabolism of plants, particularly activity that affects the water content balance of plants.

Japanese Patent Publicatiion No. 23020/1971 describes that the growth of laver in sea water is promoted by applying DL-tryptophan, L-leucine, L-cystine, L-aspartic acid, L-phenylalanine, L-tyrosine and salts of these singly or in combination.

It is an object of this invention to provide a novel plant growth promoter.

Another object of this invention is to provide a plant growth promoter comprising as an active ingredient a phenylglycine which is relatively easily available and low in cost.

Still another object of this invention is to provide a plant growth promoter having an excellent growth promoting effect and an excellent harvest increasing effect.

Yet another object of this invention is to provide a plant growth promoter which can relatively generally be applied to various plants.

A further object of this invention is to provide a method for promoting plant growth which comprises applying the plant growth promoter of the invention to a living plant or its living environment.

Other objects of the invention along with its advantages will become apparent from the following description.

According to this invention, these objects and advantages are achieved by a plant growth promoter comprising as an active ingredient for plant growth promotion at least one phenylglycine selected from the group consisting of (1) monomeric phenylglycines represented by the following formula (I)-a

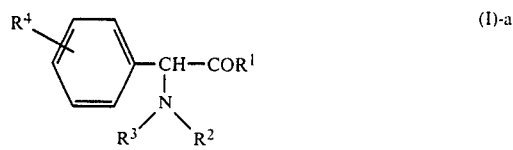

wherein
$R^1$ is $-OR^{11}$ or

in which $R^{11}$ represents a hydrogen atom or an alkyl group having not more than 5 carbon atoms, and $R^{12}$ and $R^{13}$, independently from each other, represent a hydrogen atom or an alkyl group having not more than 5 carbon atoms, or may form a 5- or 6-membered hetero-ring optionally containing a further hetero atom, together with the nitrogen atom to which they are bonded; $R^2$ and $R^3$, independently from each other, represent a hydrogen atom, an alkyl group having not more than 5 carbon atoms, or an acyl group having not more than 5 carbon atoms; and $R^4$ represents a hydrogen atom, a halogen atom, a hydroxyl group, an alkyl group having not more than 5 carbon atoms, or an alkoxy group having not more than 5 carbon atoms, salts at the carboxyl group of said phenylglycines in which $R^1$ is a hydroxyl group, and acid addition salts at the amino group of said phenylglycines in which $R^2$ or $R^3$ is other than the acyl group, (2) N-phenylglycylphenylglycines represented by the following formula (I)-b

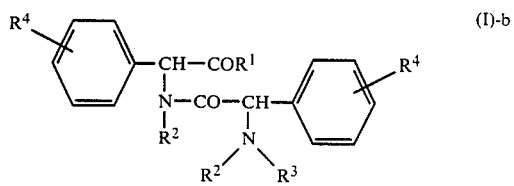

wherein
$R^1$, $R^2$, $R^3$ and $R^4$ are as defined above, salts at the carboxyl group of said n-phenylglycylphenylglycines in which $R^1$ is a hydroxyl group and acid addition salts of said N-phenylglycylphenylglycines in which $R^2$ or $R^3$ is other than the acyl group, and (3) cyclic dimers of phenylglycines represented by the following formula (I)-c

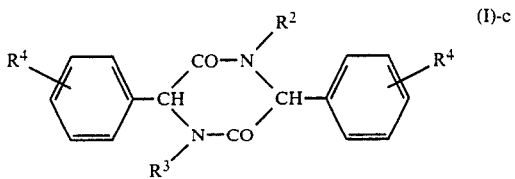

wherein

R², R³ and R⁴ are as defined above.

The compounds of formulae (I)-a, (I)-b and (I)-c have closely to do with each other because the compounds of formula (I)-a are monomeric phenylglycines, and the compounds of formulae (I)-b and (I)-c correspond to their dimers. The dimers of formula (I)-b are linear, and the dimers of formula (I)-c are cyclic.

In formula (I)-a, R¹ is —OR¹¹ or

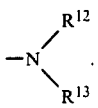

R¹¹ represents a hydrogen atom or an alkyl group having not more than 5 carbon atoms. R¹² and R¹³, independently from each other, represent a hydrogen atom or an alkyl group having not more than 5 carbon atoms. Alternatively, R¹² and R¹³, taken together, may form a 5- or 6-membered hetero-ring together with the nitrogen atom to which they are bonded. The hetero-ring may contain a further hetero atom.

The alkyl group for R¹¹ may be linear or branched, and includes, for example, methyl, ethyl, n-propyl, iso-propyl, n-butyl, sec-butyl, iso-butyl, t-butyl, and n-pentyl.

Examples of the alkyl group for R¹² and R¹³ are the same as those given above with regard to R¹¹.

The 5- or 6-membered hetero-ring formed by the combination of R¹² and R¹³ may contain a nitrogen, oxygen or sulfur atom as a further heteroatom.

According to the definition of R¹¹, examples of —OR¹¹ may include hydroxyl, methoxy, ethoxy, n-propoxy, iso-propoxy, n-butoxy and n-pentoxy.

Examples of the group

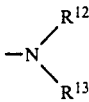

according to the definitions of R¹² and R¹³, include amino; monoalkylaminos such as methylamino, ethylamino, n-propylamino, isopropylamino n-butylamino, iso-butylamino and n-pentylamino; dialkylaminos such as dimethylamino, diethylamino and di-n-propylamino; and piperidino, piperazino, morpholino and pyridyl.

In formula (I)-a, R² and R³, independently from each other, represent a hydrogen atom, an alkyl group having not more than 5 carbon atoms, or an acyl group having not more than 5 carbon atoms. Examples of the alkyl group are the same as those given above with regard to R¹¹. Examples of the acyl group include formyl, acetyl, propionyl, butyryl, isobutyryl, valeryl and isovaleryl.

R⁴ represents a hydrogen atom, a halogen atom, a hydroxyl group, an alkyl group having not more than 5 carbon atoms, or an alkoxy group having not more than 5 carbon atoms. Examples of the halogen atom are fluorine, chlorine, bromine and iodine. Examples of the alkyl group are the same as those given above with regard to R¹¹. Examples of the alkoxy group may be the same as those given above with regard to —OR¹¹.

When the monomeric phenylglycines of formula (I)-a have a carboxyl group [when R¹ in formula (I)-a is a hydroxyl group], the carboxyl group may be in the form of a salt. Examples of the salt are salts of alkali metals such as sodium and potassium, salts of alkaline earth metals such as calcium and magnesium, and ammonium salts.

When the monomeric phenylglycines of formula (I)-a have the amino group

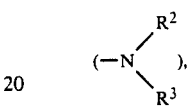

and R² or R³ is other than the acyl group, namely a hydrogen atom or an alkyl group having not more than 5 carbon atoms, the amino group may be in the form of an acid addition salt. Examples of the acid addition salt are mineral acid salts such as hydrochlorides and hydrobromides, and lower aliphatic carboxylic acid salts such as acetates.

Preferred monomeric phenyl glycines of formula (I)-a are those in which either one of R² and R³ is a hydrogen atom or an alkyl group having not more than 5 carbon atoms.

The following compounds may be cited as examples of the monomeric phenylglycines represented by formula (I)-a and their salts or acid addition salts.

(a-1) Phenylglycine,
(a-2) 4-Hydroxyphenylglycine,
(a-3) 4-Methoxyphenylglycine,
(a-4) 4-Chlorophenylglycine,
(a-5) 4-Methylphenylglycine,
(a-6) Phenylglycine methyl ester,
(a-7) Phenylglycine ethyl ester,
(a-8) Phenylglycine 2-methoxyethyl ester,
(a-9) 4-Hydroxyphenylglycine methyl ester,
(a-10) 4-Methoxyphenylglycine methyl ester,
(a-11) 4-Chlorophenylglycine methyl ester,
(a-12) 4-Methylphenylglycine methyl ester,
(a-13) N-Methylphenylglycine,
(a-14) N,N-Dimethylphenylglycine,
(a-15) N-Formylphenylglycine,
(a-16) N-Acetylphenylglycine,
(a-17) N-Trifluoroacetylphenylglycine,
(a-18) N-Acetyl-4-chlorophenylglycine,
(a-19) N-Acetyl-4-methylphenylglycine,
(a-20) N-Acetylphenylglycine methyl ester,
(a-21) Phenylglycinamide,
(a-22) 2-Amino-2-phenylacetylaminoethane
(a-23) 2-Amino-2-phenylacetylaminobutane-1,
(a-24) Phenylglycine methyl ester hydrochloride,
(a-25) 4-Hydroxyphenylglycine methyl ester hydrochloride,
(a-26) 4-Chlorophenylglycine methyl ester hydrochloride,
(a-27) 4-Methylphenylglycine methyl ester hydrochloride,
(a-28) Phenylglycine hydrochloride,
(a-29) Phenylglycine sodium salt, (a-30) 4-Chlorophenylglycine sodium salt,
(a-31) 4-Methylphenylglycine sodium salt,
(a-32) N-Acetylphenylglycine sodium salt,
(a-33) N-Acetylphenylglycine ammonium salt, and
(a-34) N-Acetylphenylglycine iso-propylammonium salt.

In formula (I)-b, the definitions of $R^1$, $R^2$, $R^3$ and $R^4$ are the same as in formula (I)-a, and specific examples of these will be apparent from the above-given examples. The N-phenylglycylphenylglycines of formula (I)-b may also be in the form of salts at the carboxyl group when $R^1$ is a hydroxyl group, or in the form of acid addition salts at the amino group when $R^2$ or $R^3$ is other than the acyl group. Examples of these salts and acid addition salts will also be apparent from the examples given above with regard to formula (I)-a.

Preferred N-phenylglycylphenylglycines of formula (I)-b are those in which $R^2$ is a hydrogen atom or an alkyl group having not more than 5 carbon atoms.

The following compounds may be cited as examples of the N-phenylglycylphenylglycines represented by formula (I)-b and their salts and acid addition salts.

(b-1) N-Phenylglycylphenylglycine,
(b-2) N-(4-hydroxyphenylglycyl)phenylglycine,
(b-3) N-(4-methoxyphenylglycyl)phenylglycine,
(b-4) N-(4-chlorophenylglycyl)phenylglycine,
(b-5) N-(4-methylphenylglycyl)phenylglycine,
(b-6) N-(4-chlorophenylglycyl)-4-chlorophenylglycine,
(b-7) N-Phenylglycylphenylglycine methyl ester,
(b-8) N-(4-hydroxyphenylglycyl)phenylglycine methyl ester,
(b-9) N-(4-methoxyphenylglycyl)phenylglycine methyl ester,
(b-10) N-(4-chlorophenylglycyl)phenylglycine methyl ester,
(b-11) N-(4-methylphenylglycyl)phenylglycine methyl ester,
(b-12) N-(4-chlorophenylglycyl)-4-chlorophenylglycine methyl ester,
(b-13) N-(N-acetylphenylglycyl)phenylglycine,
(b-14) N-(N-acetylphenylglycyl)-4-chlorophenylglycine,
(b-15) N-(N-acetylphenylglycyl)-4-methylphenylglycine,
(b-16) N-(N-acetyl-4-chlorophenylglycyl)-4-chlorophenylglycine,
(b-17) N-(N-acetylphenylglycyl)phenylglycine methyl ester,
(b-18) N-(N-acetylphenylglycyl)-4-chlorophenylglycine methyl ester,
(b-19) N-(N-acetylphenylglycyl)phenylglycinamide, and
(b-20) N-(N-acetylphenylglycyl)phenylglycine sodium salt.

In formula (I)-c, the definitions of $R^2$, $R^3$ and $R^4$ are the same as in formula (I)-a, and specific examples of these will also be apparent from the examples given hereinabove.

Preferred cyclic dimeric phenylglycines of formula (I)-c are those in which $R^2$ and $R^3$, independently from each other, represent a hydrogen atom or an alkyl group having not more than 5 carbon atoms.

The following compounds may be cited as examples of the cyclic dimers of phenylglycines represented by formula (I)-c.

(c-1) 3,6-diphenyl-2,5-piperazinedione,
(c-2) 3,6-di(4-chlorophenyl)-2,5-piperazinedione,
(c-3) 3,6-di(4-methoxyphenyl)-2,5-piperazinedione,
(c-4) 3,6-di(4-methylphenyl)-2,5-piperazinedione,
(c-5) 3-phenyl-6-(4-chlorophenyl)-2,5-piperazinedione,
(c-6) 3-phenyl-6-(4-methylphenyl)-2,5-piperazinedione, and
(c-7) 1,4-dimethyl-3,6-diphenyl-2,5-piperazinedione.

The compounds of formulae (I)-a, (I)-b and (I)-c can be produced by methods known per se [see, for example, Organic Syntheses Collective Volume 3, p. 84 (1955), and Journal of American Chemical Society, 68, 2628 (1946)].

The plant growth promoter of this invention comprises at least one phenylglycine selected from the group consisting of the monomeric phenylglycines of formula (I)-a, their salts or acid addition salts, the N-phenylglycylphenylglycines of formula (I)-b, their salts or acid addition salts, and the cyclic dimers of formula (I)-c as an active ingredient for plant growth promotion.

Usually, the plant growth promoter of this invention is used in combination with an inert carrier or adjuvant.

Examples of the inert carrier or adjuvant include solid carriers such as talc, bentonite, clay, kaolin, diatomaceous earth, white carbon, vermiculite, slaked lime, ammonium sulfate and urea; liquid carriers such as water, alcohol, dioxane, acetone, xylene, cyclohexane, methylnaphthalene and dimethylformamide; surfaceactive agents, emulsifiers or dispersants such as alkylsulfuric esters, alkylsulfonic acid salts, ligninsulfonic acid salts, polyoxyethylene glycol ethers, polyoxyethylene alkyl aryl ethers, polyoxyethylene sorbitan monoalkylates and dinaphthylmethanedisulfonic acid salts; and various adjuvants such as carboxy methyl cellulose and gum arabic. At least one such inert carrier or adjuvant may be used.

The plant growth promoter of this invention is formulated into usual formulations such as a solution, an emulsifiable concentrate, a suspension, a dust, a paste or granules by mixing it with the inert carrier and/or the adjuvant.

As the aforesaid formulations, the plant growth promoter of this invention usually contains 0.01 to 99% by weight, preferably 0.1 to 96% by weight, of the active ingredient.

The plant growth promoter of this invention promotes the growth of a plant by applying an amount, effective to promote plant growth, of it to a living plant or its living environment.

The application may be to the whole or part of the living plant body, for example its leaves, roots, stalks, buds or seeds or may be to the callus of a plant in tissue culture.

The amount, effective for plant growth promotion, of the active ingredient of the plant growth promoter of this invention is preferably 0.1 to 500 g, more preferably 1 to 200 g, per 10 ares of an area where the plant is living.

The plant growth promoter of the invention may be applied by ordinary methods such as spraying, atomizing or scattering.

In application to seeds or callus, the promoter of this invention is preferably contacted with the seeds or callus as a solution of the active ingredient in a concentration of 1 ppm to 10%, preferably 10 ppm to 1%.

The plant growth promoter of this invention has the activity of promoting the growth of various plants. It exhibits a marked growth promoting effect when applied to main cereal crops such as rice, wheat, barley, corn and soybean, sugar beet, millet, and broad-leaved crops such as radish, turnip, Japanese cabbage (pot herb mustard), Chinese cabbage, cabbage, spinach, lettuce, and water-cress.

The following Examples illustrate the present invention more specifically.

EXAMPLES 1–10

The compounds of this invention were tested for a growth promoting effect.

Ten milligrams of a test compound (each of the phenylglycine derivatives indicated in Table 1) was dissolved in 10 cc of acetone or water to form a solution (referred to as "solution A"). When solution A was an acetone solution, 3 cc of acetone and 4 cc of an aqueous solution containing 0.1% Solpor 2680 (a product of Toho Chemical Co., Ltd.) were further added to form a uniform solution (referred to as "spray solution B").

When solution A is an aqueous solution, 7 cc of an aqueous solution containing 0.1% of Solpor 2680 was added to 1 cc of solution A to form a uniform solution (referred to as "spray solution C").

Five Chinese cabbage plants, 5 Japanese cabbage plants, 2 corn plants, 5 radish plants, and 3 rice plants which had been grown in vinyl plastic pots having an area of 100 cm$^2$ for the periods indicated in the column of "DAS" in Table 1 with application of a fertilizer and were mainly in the three-leaf stage were treated with each of the spray solutions B and C by foliage application. As a control, a spray solution B having no active ingredient was prepared, and applied to the leaves of the crops. After the lapse of the periods indicated in the column of "DAT" in Table 1, the foliage portions of the crops were respectively cut off, and for each crop, the total fresh weight of the foliage portion was compared with that in the control area. The weight ratio was calculated, and the promoting effect of the compound was determined. The results are shown in Table 1.

Figure 3:
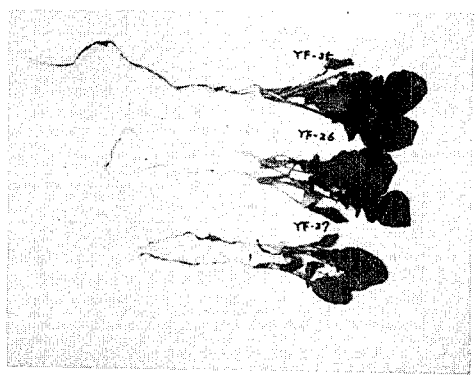

In Examples 3 and 21, the radish plants were pulled out from the pots 20 days after the foliage treatment (DAT) together with non-treated radish plants (blank) were photographed. The photo is shown in FIG. 3. In FIG. 3, the radish of Example 3 is shown at the top; the radish of Example 21, in the middle; and the non-treated radish, at the bottom.

Figure 2:

The state of growth of the Japanese cabbage in Example 5 18 days after the foliage treatment (DAT) was photographed together with non-treated Japanese cabbage (blank). The photo is shown in FIG. 2. In FIG. 2, the non-treatd Japanese cabbage (blank) is shown on the left side, and the Japanese cabbage of Example 5 (invention), on the right side.

TABLE 1

Phenylglycine derivative $$Q\text{-C}_6H_4\text{-CH(NH}_2\cdot X)\text{-COR}^1$$

| Example | Spray solution | Q*4 | X (Acid addition salt) | R$^1$ | Compound No. | Amount applied (g/10a) | Crop | DAS*2 (days) | DAT*3 (days) | Foliage weight ratio (%) | Promoting effect (%) |
| --- | --- | --- | --- | --- | --- | --- | --- | --- | --- | --- | --- |
| 1 | B | DL | — | —OCH$_3$ | a-6 | 50 | Soybean | 10 | 20 | 147 | 47 |
| 2 | B | DL | — | —OCH$_3$ | a-6 | 25 | Soybean | 10 | 20 | 149 | 49 |
| 3 | B | DL | — | —OCH$_3$ | a-6 | 50 | Radish | 10 | 20 | 213 | 113 |
| 4 | B | DL | — | —OCH$_3$ | a-6 | 25 | Rice | 10 | 20 | 128 | 28 |
| 5 | C | DL | — | —OH | a-1 | 25 | Japanese cabbage | 10 | 18 | 216 | 116 |
| 6 | B | DL | — | —O—(CH$_2$)$_2$—OCH$_3$ | a-8 | 25 | Japanese cabbage | 10 | 20 | 166 | 66 |
| 7 | C | L | — | —OH | a-1 | 25 | Japanese cabbage | 10 | 18 | 188 | 88 |
| 8 | B | DL | — | —NH(CH$_2$)$_3$CH$_3$ | a-23 | 25 | Japanese cabbage | 10 | 18 | 114 | 14 |
| 9 | B | DL | HCl | —OCH$_3$ | a-24 | 25 | Corn | 10 | 18 | 136 | 36 |
| 10 | C | DL | — | —OH | a-1 | 12.5 | Corn | 10 | 18 | 189 | 89 |
| 11 | C | DL | — | —OH | a-1 | 12.5 | Rice | 10 | 18 | 200 | 100 |
| 12 | C | D | — | —OH | a-1 | 25 | Rice | 10 | 18 | 155 | 55 |
| 13 | C | D | — | —OH | a-1 | 12.5 | Rice | 10 | 18 | 173 | 73 |
| 14 | C | L | — | —OH | a-1 | 25 | Rice | 10 | 18 | 164 | 64 |
| 15 | C | L | — | —OH | a-1 | 12.5 | Corn | 10 | 18 | 168 | 68 |
| 16 | B | D | HCl | —OCH$_3$ | a-24 | 25 | Rice | 10 | 18 | 182 | 82 |
| 17 | C | DL | — | —O—Na | a-29 | 25 | Japanese cabbage | 14 | 20 | 108 | 8 |
| 18 | C | L | — | —OH | a-1 | 25 | Chinese cabbage | 14 | 20 | 140 | 40 |
| 19 | C | L | — | —OH | a-1 | 25 | Corn | 14 | 20 | 125 | 25 |
| 20 | B | DL | — | —OCH$_3$ | a-6 | 25 | Potato | 10 | 20 | 212*1 | 112 |
| 21 | B | DL | — | —OCH$_3$ | a-6 | 25 | Radish | 10 | 20 | 181 | 81 |

*1 Weight ratio of the rhizomes.
*2 DAS means days after seeding.
*3 DAT means days after treatment.
*4 Q shows optical activity.

EXAMPLES 22 AND 23

Treatment of seeds by L-phenylglycine

Ten milligrams of L-phenylglycine was dissolved in 100 cc of water in a concentration of 100 ppm. Ten seeds of corn or 20 seeds of Chinese cabbage were immersed in the solution overnight (for 15 hours). Thereafter, three seeds of corn and 10 seeds of Chinese cabbage so treated were sown in vinyl plastic pots having a surface area of 100 cm$^2$ and filled with soil. On the 18th day, the foliage portions of the plants were cut off and their fresh weight was measured.

As a control, seeds of corn and seeds of Chinese cabbage not subjected to the immersion treatment were sown, and on the 18th day, their foliage portions were cut off and their total fresh weight was measured in the same way as above.

The ratio of the weight of the foliage portion to that of the foliage portion in the control was calculated.

The results are shown in Table 2.

TABLE 2

| Example | Crop | Foliage weight ratio (%) | Promoting effect (%) |
|---|---|---|---|
| 22 | Chinese cabbage | 135 | 35 |
| 23 | Corn | 120 | 20 |

EXAMPLE 24

Synthesis of N-(N-acetylphenylglycyl)phenylglycine methyl ester

To 20 parts by volume of chloroform was added 0.96 part by weight of N-acetylphenylglycine. With ice cooling, 1.03 parts by weight of dicyclohexylcarbodiimide was added, and the mixture was stirred. Furthermore, 0.83 part by weight of phenylglycine methyl ester was added, and about 3 hours later, the temperature was returned to room temperature. The mixture was then stirred overnight. After the reaction, the precipitate was collected by filtration, and washed with chloroform. The filtrate was concentrated to dryness. The resulting solid was washed with ethyl acetate, and extracted with a mixture of chloroform and petroleum ether to give 1.2 parts by weight of the captioned compound having a melting point of 198° to 200° C.

EXAMPLE 25

Synthesis of 3,6-diphenyl-2,5-piperazinedione

Four parts by weight of phenylglycine methyl ester was heated at 200° C. for 1 hour in an atmosphere of nitrogen with stirring. After the reaction, the reaction mixture was washed successively with acetone, water and acetone in this order, and dried under reduced pressure. The crude product was recrystallized from dimethylformamide to obtain 2.7 parts by weight of 3,6-diphenyl-2,5-piperazinedione having a melting point of 282° to 284° C.

EXAMPLES 26-35

Test of 3,6-diphenyl-2,5-piperazinedione for a plant growth promoting effect

One part by weight of 3,6-dipenyl-2,5-piperazinedione synthesized in Example 25, 8.7 parts by weight of a mixture of equal amounts of talc and bentonite, and 0.3 part by weight of a mixture of equal amounts of Solpor 5060 (a product of Toho Chemical Co., Ltd.) and Solpor 800A (a product of Toho Chemical Co., Ltd.) were well pulverized and mixed to form a wettable powder.

Cabbage, Japanese cabbage, lettuce and corn (5 plants each) which had been grown for 2 weeks after sowing in vinyl plastic pots having an area of 100 cm² with the application of a fertilizer and were in the 3 to 4 leaf stage were sprayed with the wettable powder diluted with water to each of the 3,6-diphenyl-2,5-piperazinedione concentrations shown in Table 3. After the lapse of three weeks from the spraying treatment, the foliage portions were cut off and their total fresh weight was compared with that in a non-treated control area, and the weight ratio was calculated. The results are shown in Table 3.

The state of growth of Chinese cabbage in Example 28 two weeks after the foliage treatment (DAT) was photographed together with non-treated Chinese cabbage, and the photo is shown in FIG. 1. In FIG. 1, the non-treated Chinese cabbage is shown on the left, and the treated Chinese cabbage (Example 28), on the right.

Figure 4:
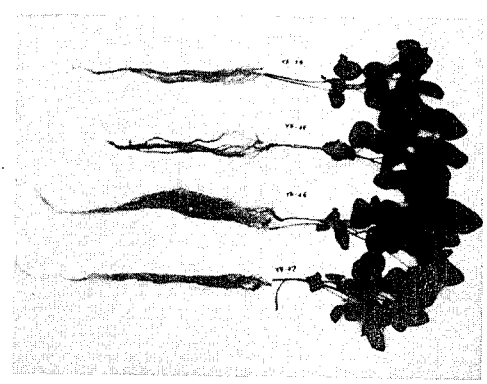

The sobybean plants in Examples 33 to 35 were respectively pulled out from the pots two weeks after the foliage treatment (DAT), and photographed together with non-treated soybean plant (blank). The photo is shown in FIG. 4. From top to bottom in FIG. 4, the non-treated plant (blank) is shown in the first place; the treated plant of Example 33, in the second place; the treated plant of Example 34, in the third place; and the treated plant of Example 35, in the fourth place (bottom).

TABLE 3

| Example | Amount applied (g/10a) | Crop | Foliage weight ratio (%) | Promoting effect (%) |
|---|---|---|---|---|
| 26 | 50 | Chinese cabbage | 199 | 99 |
| 27 | 50 | Japanese cabbage | 166 | 66 |
| 28 | 25 | Chinese cabbage | 200 | 100 |
| 29 | 25 | Japanese cabbage | 155 | 55 |
| 30 | 25 | Lettuce | 178 | 78 |
| 31 | 25 | Corn | 123 | 23 |
| 32 | 12.5 | Japanese cabbage | 178 | 78 |
| 33 | 25 | Soybean | 148 | 48 |
| 34 | 50 | Soybean | 202 | 102 |
| 35 | 100 | Soybean | 175 | 75 |

EXAMPLES 36-44

Chinese cabbage, Japanese cabbage, lettuce and radish which were grown in an outdoor field having an area of 0.5 m² for 2 weeks after sewing and were in the 4 to 5 leaf stage were sprayed with the wettable powder prepared in Examples 26 to 35 and diluted to each of the 3,6-diphenyl-2,5-piperazinedione concentrations indicated in Table 4. Forty days after the spraying treatment, the foliage portion was cut off and its total fresh weight was compared with that in a non-treated control area. The weight ratio was calculated, and the promoting effect was measured. The results are shown in Table 4.

TABLE 4

| Example | Amount applied (g/10a) | Crop | Foliage weight ratio (%) | Promoting effect (%) |
|---|---|---|---|---|
| 36 | 50 | Japanese cabbage | 245 | 145 |
| 37 | 50 | Lettuce | 168 | 68 |
| 38 | 50 | Radish | 182 | 82 |
| 39 | 25 | Chinese cabbage | 118 | 18 |
| 40 | 25 | Japanese cabbage | 118 | 18 |
| 41 | 25 | Lettuce | 183 | 83 |
| 42 | 25 | Radish | 110 | 10 |
| 43 | 12.5 | Chinese cabbage | 152 | 52 |

TABLE 4-continued

| Example | Amount applied (g/10a) | Crop | Foliage weight ratio (%) | Promoting effect (%) |
| --- | --- | --- | --- | --- |
| 44 | 12.5 | Radish | 139 | 39 |

EXAMPLES 45-60

Japanese cabbage, corn, soybean and radish were sown in the same pots as in Examples 1 to 20 in the same way as in Examples 1 to 20. Fourteen days after sowing, each of the compounds shown in Table 5 (the compound numbers correspond to those shown in the specification) in the form of each of the spray solutions indicated in Table 5 was applied to the plants through foliage.

In the column of "spray solution" in Table 5, "B" and "C" were prepared as in Examples 1 to 20; and the "wettable powder (WP for short)" was prepared as in Examples 26 to 35.

Separately, the crops were grown as a control without applying these compounds.

Twenty days after the foliage treatment (DAT), the foliage portion of each of the crops was cut off and its total fresh weight was compared with that in the control. The weight ratio was calculated, and the promoting effect was measured.

The results are summarized in Table 5.

TABLE 5

| Example | Compound No. | Spray solution | Amount applied (g/10a) | Crop | DAS (days) | DAT (days) | Foliage weight ratio (%) | Promoting effect (%) |
| --- | --- | --- | --- | --- | --- | --- | --- | --- |
| 45 | a-2 | WP | 50 | Japanese cabbage | 14 | 20 | 178 | 78 |
| 46 | a-25 | C | 50 | Corn | 14 | 20 | 112 | 12 |
| 47 | a-9 | B | 50 | Japanese cabbage | 14 | 20 | 155 | 55 |
| 48 | a-4 | WP | 50 | Japanese cabbage | 14 | 20 | 129 | 29 |
| 49 | a-26 | C | 50 | Soybean | 14 | 20 | 108 | 8 |
| 50 | a-11 | B | 50 | Corn | 14 | 20 | 115 | 15 |
| 51 | c-2 | WP | 50 | Radish | 14 | 20 | 133 | 33 |
| 52 | c-2 | WP | 50 | Japanese cabbage | 14 | 20 | 158 | 58 |
| 53 | a-5 | WP | 50 | Japanese cabbage | 14 | 20 | 235 | 135 |
| 54 | a-5 | C | 50 | Corn | 14 | 20 | 108 | 8 |
| 55 | a-5 | B | 50 | Corn | 14 | 20 | 121 | 21 |
| 56 | c-4 | WP | 50 | Japanese cabbage | 14 | 20 | 209 | 109 |
| 57 | c-4 | WP | 50 | Corn | 14 | 20 | 191 | 91 |
| 58 | a-16 | WP | 50 | Japanese cabbage | 14 | 20 | 112 | 12 |
| 59 | b-17 | WP | 50 | Japanese cabbage | 14 | 20 | 108 | 8 |
| 60 | a-34 | WP | 50 | Japanese cabbage | 14 | 20 | 212 | 112 |

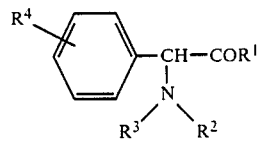

(I)-a wherein
$R^1$ is $-OR^{11}$ or

in which $R^{11}$ represents a hydrogen atom or an alkyl group having not more than 5 carbon atoms, and $R^{12}$ and $R^{13}$, independently from each other, represent a hydrogen atom or an alkyl group having not more than 5 carbon atoms; $R^2$ and $R^3$, independently from each other, represents a hydrogen atom, an alkyl group having not more than 5 carbon atoms, or an acyl group having not more than 5 carbon atoms; and $R^4$ represents a hydrogen atom, a halogen atom, a hydroxyl group, an alkyl group having not more than 5 carbon atoms, or an alkoxy group having not more than 5 carbon atoms, salts at the carboxyl group of said phenylglycines in which $R^1$ is a hydroxyl group, and acid addition salts at the amino group of said phenylglycines in which $R^1$ is a hydroxyl group, and acid addition salts at the amino group of said phenylglycines in which $R^2$ or $R^3$ is other than the acyl group, to a living plant or its environment.

2. The method of claim 1 wherein the amount effective for plant growth promotion is 0.1 to 500 g per 10 ares of an area where the plant is living.

What is claimed is:

1. A method of plant growth promotion which comprises applying an amount effective for plant growth promotion of at least one monomeric phenylglycine of the following formula (I)-a

* * * * *